United States Patent [19]

Stoop et al.

[11] Patent Number: 5,549,647
[45] Date of Patent: Aug. 27, 1996

[54] PACEMAKER WITH IMPROVED FAR FIELD R WAVE SENSING AND SUPPRESSION

[75] Inventors: Gustaaf A. P. Stoop, Dieren; Marijn van Gemert, Nijmegen; Paul V. van Zanten, Arnhem, all of Netherlands

[73] Assignee: Vitatron Medical, B.V., Dieren, Netherlands

[21] Appl. No.: 318,050

[22] Filed: Oct. 4, 1994

[51] Int. Cl.⁶ .................................................. A61N 1/362
[52] U.S. Cl. ................................................................ 607/9
[58] Field of Search .......................... 607/14, 15; 128/705

[56] References Cited

U.S. PATENT DOCUMENTS

| | | | |
|---|---|---|---|
| 4,284,082 | 8/1981 | Funke et al. | 128/419 PG |
| 4,407,287 | 10/1983 | Herpers | 128/419 PG |
| 4,513,752 | 4/1985 | Weyant | 128/696 |
| 4,539,991 | 9/1985 | Boute et al. | 128/419 PG |
| 4,554,921 | 11/1985 | Boute et al. | 128/419 PG |
| 4,920,965 | 5/1990 | Funke et al. | 128/419 PG |
| 5,065,759 | 11/1991 | Begemann et al. | 128/419 PG |
| 5,193,550 | 3/1993 | Duffin | 128/697 |
| 5,247,929 | 9/1993 | Stoop et al. | 607/14 |
| 5,400,796 | 3/1995 | Wecke | 128/705 |

*Primary Examiner*—William E. Kamm
*Attorney, Agent, or Firm*—Woodcock Washburn Kurtz Mackiewicz & Norris

[57] ABSTRACT

A dual chamber pacemaker is provided with a dynamic PVARP which tracks the occurrence of high rate atrial senses within the normal PVARP range. The dynamic PVARP is a short window of about 50 ms which is moved toward the time of occurrence of any sense signal within the window range of about 50–200 ms following the ventricular event. Senses which occur within the dynamic window are rejected, or blanked, while senses occurring within the window range but outside of the window are recognized and evaluated. The dynamic window technique accordingly enables the pacemaker to recognize tachycardia senses which would otherwise be blanked by a fixed length PVARP, while providing efficient suppression of FFRS events. The pacemaker also provides a technique for determining whether rejected senses are tachy atrial senses or FFRS, by modulating the AV interval and thus shifting the dynamic window which is coupled to the ventricular pulse. As a result of this modulation, FFRS events move with the dynamic window, but tachy senses are covered, or revealed, enabling the pacemaker to make an appropriate response.

21 Claims, 6 Drawing Sheets

PACEMAKER WITH IMPROVED FAR FIELD R WAVE SENSING AND SUPPRESSION

BACKGROUND OF THE INVENTION

1. Field of the Invention

This invention relates to cardiac pacing systems and, more particularly, to dual chamber pacing systems designed to optimize the sensing of tachycardia atrial senses while rejecting far field R wave senses.

2. Description of the Prior Art

The advantages of dual chamber pacing are now well recognized in the art. Since the dual sense-dual pace DDD pacemaker became commercially available, it has gained favor for the reason that it compensates for many of the disadvantages of other pacemaker modes. The classic DDD pacemaker is described in U.S. Pat. Nos. 4,920,965, 4,539,991 and 4,554,921, incorporated herein by reference. In such a DDD pacemaker, or a VDD pacemaker, atrial events are sensed, allowing natural or physiological P-waves to synchronously control the ventricular pacing rate. An area of dual chamber pacemakers that has received a great deal of attention in the pacemaker industry is that of dealing with high atrial rates. If high atrial rates can be recognized, the pacemaker can optimize synchronous tracking but also be able to recognize atrial tachycardia and take appropriate responses when such tachycardia occurs. It is known, of course, to provide a Wenckebach-type response which provides a degree of synchronization for high rates and maintains the ventricular stimulus rate within an upper rate limit.

Another means of responding to high rate atrial signals, whether or not premature atrial contractions, is to extend the post-ventricular atrial refractory period (PVARP). Likewise, the atrial refractory time can be extended past the time of anticipated retrograde P-waves to avoid sensing of such retrograde P-waves, so as to avoid pacemaker-mediated tachycardia. It is also known to vary PVARP as a function of sensor data. See also Funke, U.S. Pat. No. 4,920,965, where the atrial pacing timeout and effective PVARP are varied as a function of certain sensed signals. However, the extension of PVARP or the atrial refractory period lowers the upper rate limit for sensing atrial signals, and thus reduces the capability of the pacemaker to provide synchronous operation in response to high rate atrial heartbeats which may yet be physiological.

Another approach is to reduce to PVARP as much as possible, in order to enhance detection of high rate atrial signals. However, this makes a VDD or DDD pacemaker more vulnerable to far field R wave senses (FFRS). An FFRS following a ventricular pace (VP) is known to occur within an interval of up to about 180 ms from the VP, while an FFRS following a ventricular sense (VS) occurs within a shorter interval (e.g. 0–100 ms). An extension of PVARP to >100 or 180 ms, in order to blank or reject a potential FFRS, is contrary to the objective of minimizing PVARP as much as possible in order to be able to sense, or "see" as many high rate atrial signals as possible.

U.S. Pat. No. 5,247,929, assigned to the same assignee as this invention and incorporated by reference, discloses a dual chamber pacemaker which includes a VA conduction test for concurrently testing for the conditions of retrograde conduction (RC) and FFRS. In this patent, the pacemaker changes the AV or VV interval to a predetermined interval over a number of pacemaker cycles, and determines whether the VA interval remains substantially unchanged, i.e., whether the VA intervals are substantially equal. When VA interval equality is determined, the pacemaker checks the measure of VA interval with stored RC and FFRS criteria to determine whether either can be verified. However, for FFRS detection, this procedure demands an extended period of atrial sensing following the ventricular pacing. Such condition is generally met in the case of retrograde conduction, but often is not found in the case of far field sensing. Accordingly, what is needed is a more effective technique which captures (identifies) and suppresses incidentally sensed far field signals, while blanking of real atrial signals (P-waves) is avoided as much as possible.

SUMMARY OF THE INVENTION

The above object is achieved by a pacemaker with a dynamic PVARP window, which window is movable within a defined PVARP range, e.g., 50–200 ms. The dynamic window tracks high rate atrial senses, e.g., P-waves or FFRS, which occur within the PVARP range, so that high rate signals which occur with substantially the same timing will fall within the window. By making the window relatively short in duration, e.g., 50 ms, most FFRS events are captured in the window and rejected, while tachy P-waves that fall within the range but outside the window are recognized and accepted for interpretation. Since it is recognized that some stable rate P-waves can nevertheless be captured in the dynamic window, the pacemaker provides for modulating the window in a way so as to determine whether captured senses are FFRS or P-waves.

BRIEF DESCRIPTION OF THE DRAWINGS

FIGS. 5c and 5d are timing diagrams showing how an FFRS follows the dynamic window after AV modulation.

DESCRIPTION OF THE PREFERRED EMBODIMENTS

Figure 1:
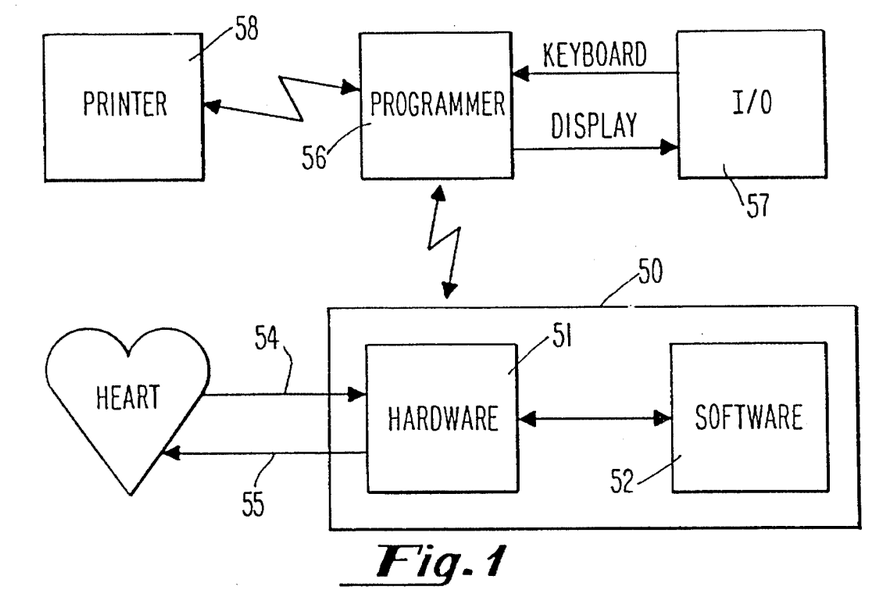
FIG. 1 is a block diagram of the overall pacemaker system of the invention, showing the environment in which the pacemaker software operates.
Figure 3A:
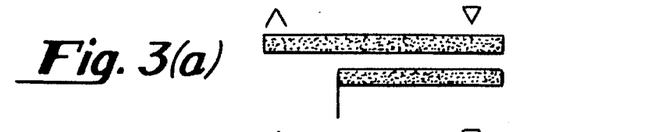
FIG. 3a is a timing diagram illustrating a fixed PVARP.
Figure 4:
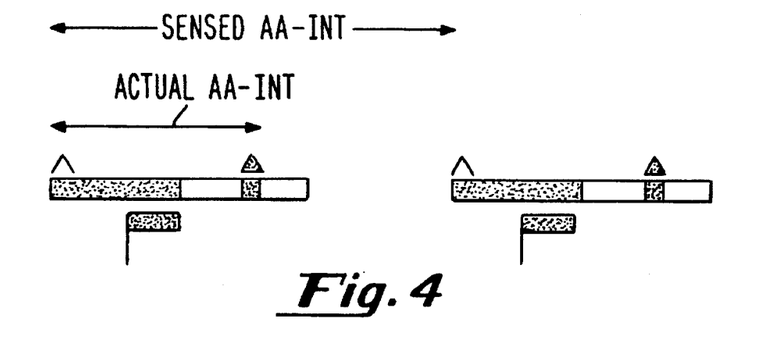
FIG. 4 is a timing diagram showing the possibility blanking tachy senses by the dynamic blanking window of this invention.
Figure 5A:
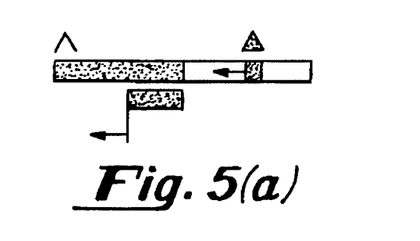
FIGS. 5a and 5b are timing diagrams showing the effect of AV modulation on the timing of tachy senses relative to the dynamic window.
Figure 5B:
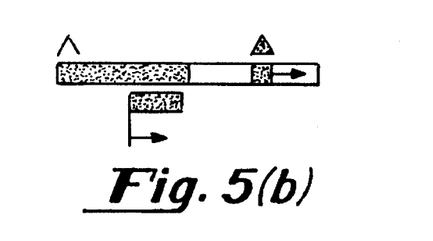
Figure 5C:
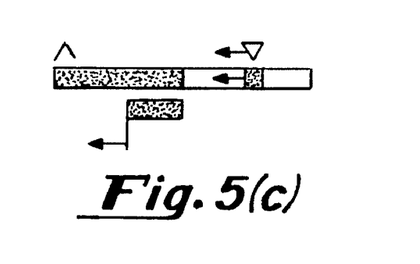

The timing diagrams which are used to illustrate functions, as seen in FIG. 5.3a–6, are the equivalent of flow charts in showing the logical steps carried out by the software in response to parameters that control the pacing behavior. These timing diagrams correspond to the IEEE 830-1984 standard for software requirement specifications. The pacing system of this invention is software-based, i.e., the software controls all functions through the hardware, as illustrated in FIG. 1. Further referring to FIG. 1, the pacemaker 50 is shown as having a component hardware portion 51 and a software portion 52, the two portions being interconnected. The software is parameter-driven, i.e., there are numerous parameters that control the pacing behavior, diagnostic functions, etc. The hardware is interconnected with the patient's heart by one or more electrodes 55, and one or more sensor connections 54. As is well understood in the art, for a dual chamber pacemaker, there are generally two leads, an atrial lead and a ventricular lead each lead having at least one electrode unipole or bipole positioned in the heart. The line 54 is illustrated as leading to the heart, as in a QT-type sensor arrangement, but may be attached to the outside case of the pacemaker or may couple to any other available sensor for sensing body parameter information used in rate responsive pacing systems. Further, in the preferred embodiment of the pacing system of this invention, sensor link 54 may comprise a pair of sensors, e.g., QT plus activity, as set forth in U.S. Pat. No. 5,065,759.

As further illustrated in FIG. 1, the pacer 50 is in telemetric communication with a programmer 56. The user can select parameters and program them through programmer 56, and can also interrogate parameter and diagnostic data from the implanted pacemaker. Interrogated information from the pacer can be coupled by telemetry directly to a printer 58. Input/output devices 57 are used to input information by the user to the programmer, or to display information received by the programmer from the pacemaker.

Figure 2:
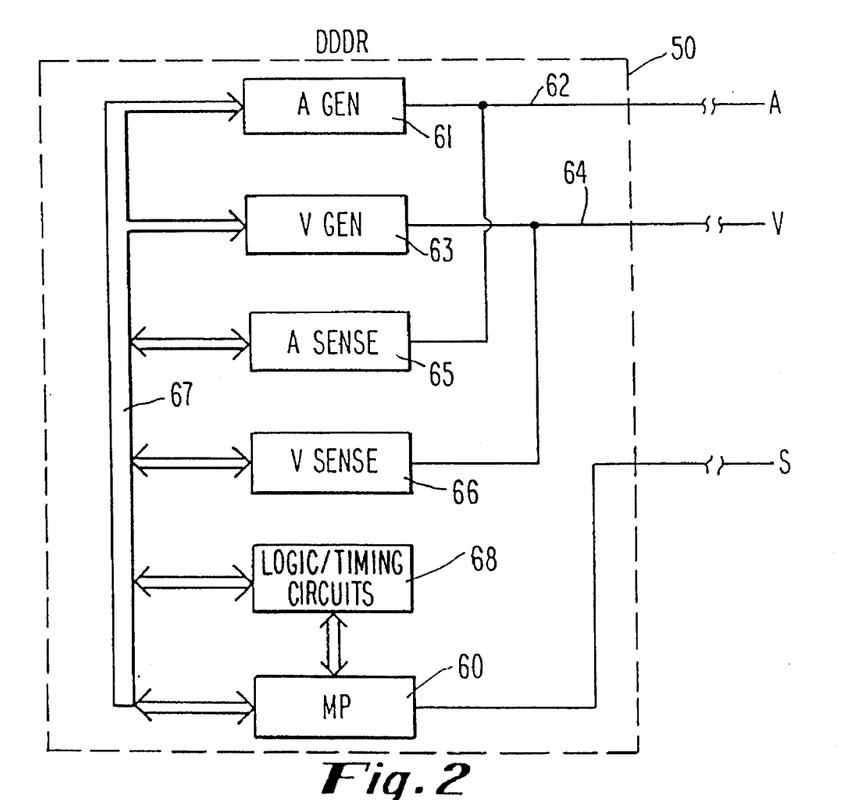
FIG. 2 is a block diagram which illustrates basic components of the pacemaker of this invention together with leads and a sensor for delivering signals to and/or receiving signals from the patient.

Referring to FIG. 2, there is shown a basic block diagram of primary hardware components of a DDDR pacer 50. An atrial generator 61 is shown, having an output connected to lead 62 which communicates with the patient's atrium. An A sense amplifier 65 is illustrated also connected to atrial lead 62. A ventricular generator 63 is illustrated which is connected to the patient's ventricle through lead 64. V sense amplifier 66 is also connected to lead 64, to receive and sense signals from the patient's ventricle. Generators 61 and 63 and sense blocks 65 and 66 are interconnected with microprocessor system 60, which microprocessor has software which is parameter-driven to control the operation of the hardware units. Microprocessor system 60 may be interconnected with hardware logic and/or timing circuits 68. The microprocessor system consists of a suitable microprocessor and accompanying ROM and RAM memory. In a manner well known in the art, the software contains a number of strategic places where escape points to a RAM routine are available. As affects the scope of this invention, the degree to which software supplants hardware, or vice versa, is a matter of design choice. Thus, for the many timing functions that are carried out in the pacing system of this invention, it is to be understood that the microprocessor may have built in timing circuits, or suitably may control external hardware timer circuits. Software control of pacing function is well known in the art, such that the following detailed discussions of the software specifications enable one of ordinary skill in this art area to design a system for carrying out the functions within the scope of the invention. Data inputted from programmer 56 is stored in memory associated with the microprocessor.

Still referring to FIG. 2, there is shown a sensor S, indicated as providing an input to microprocessor system 60. Sensor S represents one or more sensors for monitoring one or more body parameters known to be indicative of desired pacing rate. Sensor S is illustrated as being outside the pacemaker, but may be physically located inside the pacemaker casing, as with certain activity sensors. Alternately, as is the case with the Q-T-type rate responsive pacemaker, the "sensor" information is actually obtained from the ventricular lead, by extracting timing information relating to the Q-T interval. As used in the practice of this invention, the term sensor or sensor signal may refer to information obtained from any available rate responsive sensor-type source. Also, as used in the claims hereto, the term "rate signal" may refer to a signal deriving its information from either or both a sensor source and the sensed atrial rate. It is to be noted that the invention can also be applied to a VDDR pacemaker.

A standard approach for preventing a dual chamber pacemaker from sensing and acting on far field R-waves (FFRS) is to provide a post-ventricular atrial refractory period (PVARP). As illustrated in FIG. 3(a), the PVARP extends for a predetermined time duration following the ventricular pace, e.g. 200 ms. In a further adaptation, the length of the PVARP is adapted to measure FFRS intervals, so that in theory it is adjusted periodically to extend just past the time when an FFRS is expected to come. As stated above, however, this approach presents a problem in a dual chamber pacemaker in which it is an objective to optimize detection of atrial tachycardia. It is understood that in order to optimize detection of atrial tachycardia, it is desirable ideally to have no PVARP, so as to be able to sense, or "see" all atrial events. In such a pacemaker, the decision as how to respond to a high rate atrial sense is, of course, important, and such response can take any number of different forms. However, what is important to this invention is the need in the pacing art to provide a dual chamber pacemaker which sees essentially all atrial senses, i.e., blanks out as few as possible but which at the same time is able to suppress any occurrence of FFRS.

Reference is made to the aforementioned U.S. Pat. No. 5,247,929, incorporated herein by reference, for showing a dual chamber pacemaker utilizing decision rates, including a dynamic tracking limit and dynamic pacing limit and the conditions which enable synchronous pacing. The incorporated patent also discloses the use of an atrial sync pulse (ASP) following early atrial senses, for the purpose of attempting to regain synchronous tracking operation. As used in the claims appended hereto, the term atrial sense (AS) can mean a P-wave, an FFRS, or any signal picked up from an electrode in the area of a patient's atrium.

Figure 3B:
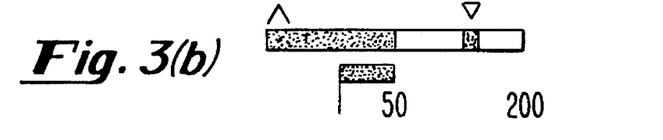
FIG. 3b is a timing diagram illustrating the dynamic PVARP of this invention, and the blanking of an FFRS.

The basic technique provided by this invention is shown in FIG. 3(b), which illustrates a dynamic PVARP. In the approach of this invention, a small duration dynamic window is employed instead of a fixed length PVARP. After a certain learning period by the pacemaker, starting at implantation, the fixed PVARP is switched to a minimum period of 50 ms, and the dynamic blanking window becomes active. This blanking window has a duration typically about 50 ms, but may be programmed to any desired duration between 0 and 200 ms. The window is continually adjusted by the pacemaker to move in the direction where atrial senses have recently occurred within a predetermined window range. The range of the window is illustrated as being between 50 and 200 ms following the ventricular pace (VP). This window range, or length, is programmable in order to adapt to the FFRS variability of a given patient. In practice, any atrial sense (AS) from whatever source that occurs within this window is blanked, i.e., it is rejected and not utilized by the pacemaker. Assuming that most senses which occur within the dynamic blanking window range would be FFRSs, then such FFRSs would be blanked whereas as high rate P-waves, outside of the window but within the window range, would be sensed and interpreted by the pacemaker. In this way, the effective atrial blanking is minimized and adapted to the FFRS. It is to be understood that in most cycles, and indeed the great percentage of cycles, there would be no FFRS. Under these conditions, the dynamic blanking window remains active, but is substantially static, i.e., it is not moved. Of course, normal physiologic P-waves that occur after the window range, e.g., after 200 ms, are not used to adjust the window.

Figure 11:
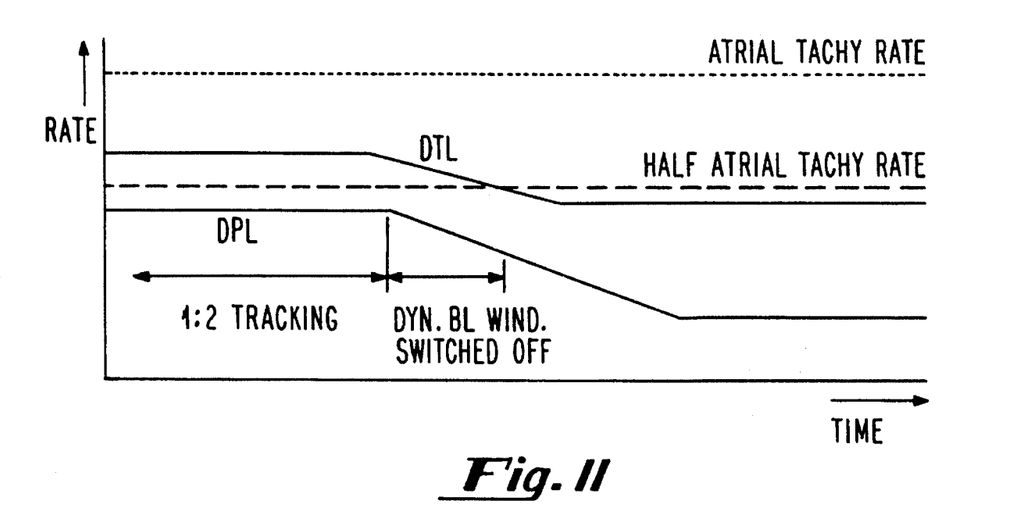
FIG. 11 is a rate diagram illustrating how 1:2 tracking is avoided by switching off the dynamic blanking window.

While the dynamic blanking window is designed to suppress FFRS, it is unavoidable that in a small number of instances true P-waves (originated by PACs or high atrial rates) will fall within the dynamic window and be blanked. Specifically, if an atrial tachycardia is detected and the pacemaker has a flywheel mode, the ventricle will be paced at the flywheel rate, or pacing limit. As seen in reference to FIG. 11, if the flywheel rate is decremented to a lower pacing limit, the half-atrial tachy rate may fall within the tracking range, between DPL and DTL. If this occurs, there may be a situation where every second atrial sense is captured and blanked by the dynamic blanking window. As seen in FIG. 4, if a first tachy P-wave happens to coincide with the dynamic blanking window, and the tachy rate remains substantially constant, every other P-wave will fall within the dynamic window and be blanked, resulting in 1:2 tracking. This phenomenon is known to be inherent for any PVARP, and while less likely could also occur with the dynamic blanking window. In this situation, it would be desirable for the pacemaker to be able to determine that P-waves were present, i.e., there was tachy, so that the pacemaker could respond in a desired way.

A solution to the above problem is derived from the observation that the dynamic blanking window is coupled to the ventricular pace pulse, e.g, the blanking window is adjusted to be centered relative to delivery of the VP. It follows that by either lengthening or shortening the AV delay, P-waves that were being blanked would be effectively shifted out of the window, whereas FFRS events would remain coupled with the window. Referring to FIG. 5a, there is shown a sequence of constant rate P-waves where the AV delay is shortened. By moving the synchronized VP forward in time, the window is moved forward to a time prior to the next occurring P-wave, thus revealing the P-wave. Likewise, as seen in FIG. 5b, if the AV delay is lengthened, the blanking window occurs only after the atrial sense. In either event, modulation of the AV delay changes the relative timing of the P-wave and the dynamic blanking window, thereby revealing the presence of underlying tachy. By contrast, FIGS. 5c and 5d show the situation for FFRS, which remains coupled to the VP. Whether AV delay is shortened as in FIG. 5c, or lengthened as in FIG. 5d, the FFRS follows the AV variation, and continues to be blanked. Accordingly, it is seen that whenever the pacemaker recognizes that a sense has been captured within the dynamic blanking window, subsequent modulation of the AV delay can be performed to determine whether a high rate P-wave or an FFRS has occurred.

Figure 6:
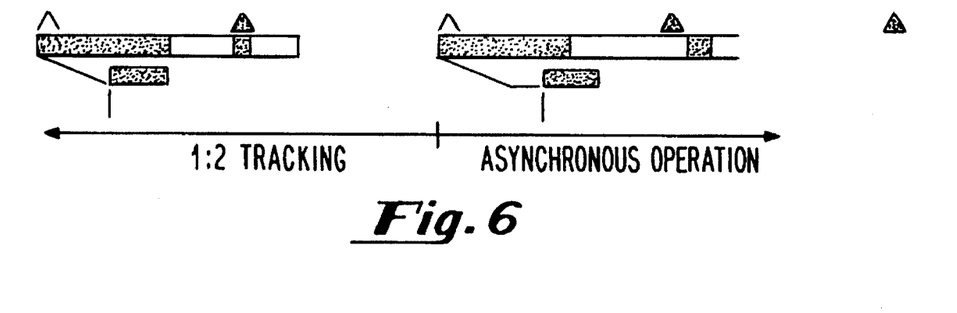
FIG. 6 is a timing diagram illustrating how AV extension results in modulating the dynamic window so as to reveal a tachy sense, resulting in asynchronous operation.
Figure 6D:
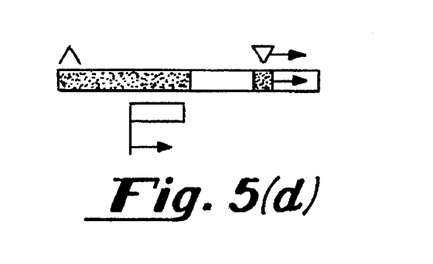

In FIG. 6, the effect of AV lengthening in the case of 1:2 tracking of an atrial tachycardia is illustrated (it being assumed that FFRS is absent). The first P-wave results in a tracked VP occurring after a normal AV interval. The next AS is shown to coincide with the dynamic blanking window, and is accordingly blanked, resulting in 1:2 tracking. The next P-wave is sensed, and the AV interval is extended, as illustrated. Accordingly, it is seen that the dynamic blanking window has shifted to the right, or after the occurrence of the next P-wave, such that the P-wave is recognized as tachycardia. Upon tachy recognition, the pacemaker suitably goes into asynchronous operation, i.e., does not track the excessively high rate AS. Alternately, synchronous operation can be maintained or re-established, as by delivering an atrial sync pulse (ASP). See referenced U.S. Pat. No. 5,247,929 for a discussion of the ASP technique.

Figure 7:
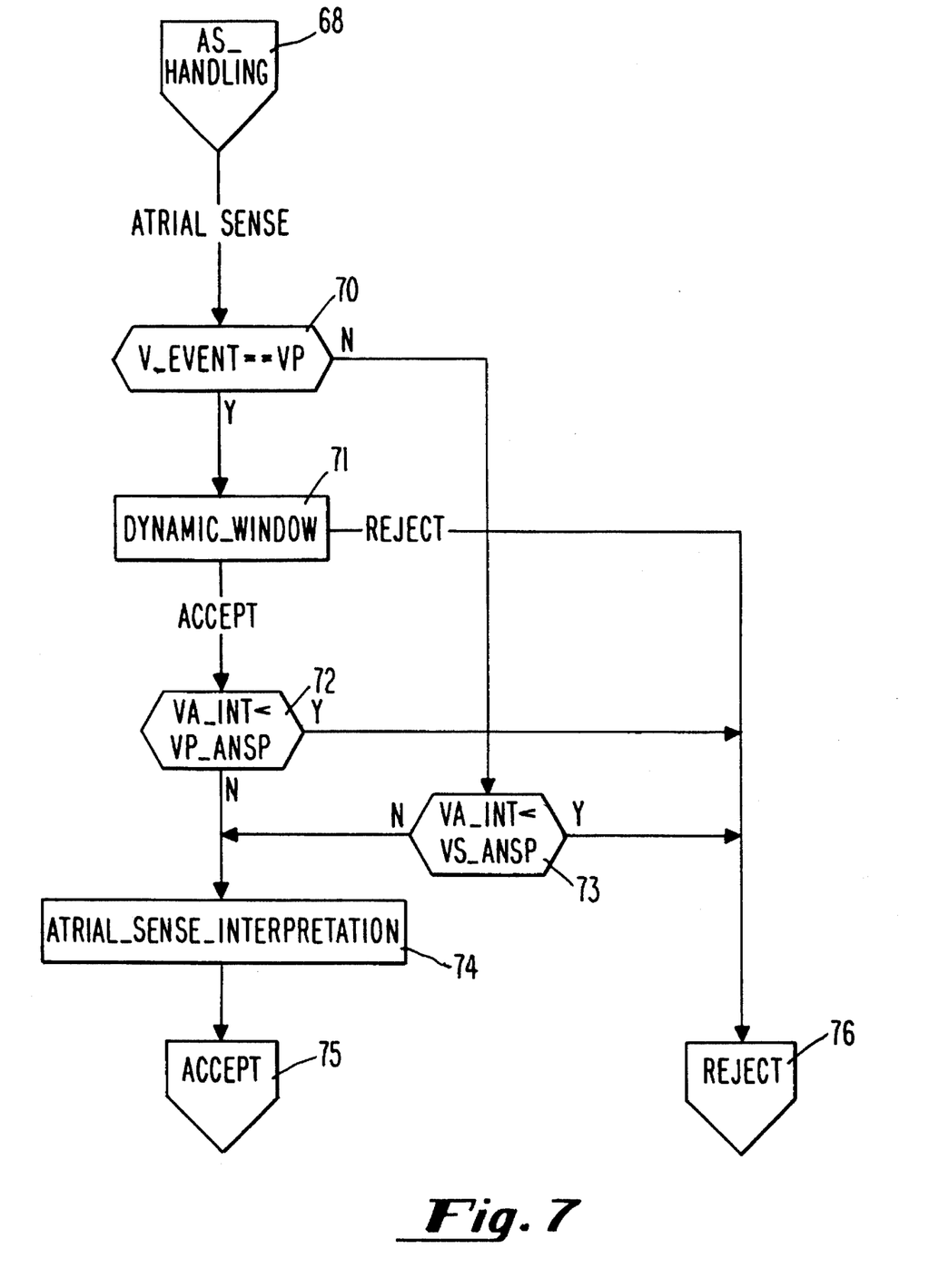
FIG. 7 is a flow diagram illustrating broadly the steps of determining whether an atrial sense is accepted or rejected, including determining when a dynamic window adjustment is made.

Referring now to FIG. 7, there is shown a simplified flow diagram which shows the relation of the dynamic window routine with respect to the sequence of receiving and interpreting an atrial sense. At block 68, a sensed atrial signal is processed, which includes determining the VA interval. When an atrial sense has been found and processed, the pacemaker determines at 70 whether the prior ventricular event was a ventricular pulse. If no, meaning that it was a ventricular sense, the routine branches to block 73 and determines whether the VA interval is less than the atrial non-sensing period following a VS. This is a constant period, set just greater than the expected time for an FFRS following a VS, e.g., 100 ms. If yes, then the atrial sense must be rejected. If the answer at 73 is no, the program branches to block 74 and interprets the atrial sense, i.e., classifies it. The routine exits at 75 under conditions that the atrial sense has been accepted. Returning to block 70, if the prior ventricular event was a VP, then the routine goes to block 71 and carries out the dynamic window subroutine, which is discussed in more detail in connection with FIG. 8. As a result of this subroutine, the atrial sense is either accepted or, if it is found to be within the dynamic window, it is rejected. If accepted, it is determined at 72 whether the VA interval is less than the atrial non-sensing period following a VP, e.g., less than 50 ms. If yes, the atrial sense cannot be accepted, and the routine exits at 76, rejecting the atrial sense. If the answer at 72 is no, then the routine proceeds to block 74 and interprets the accepted atrial sense.

Figure 8:
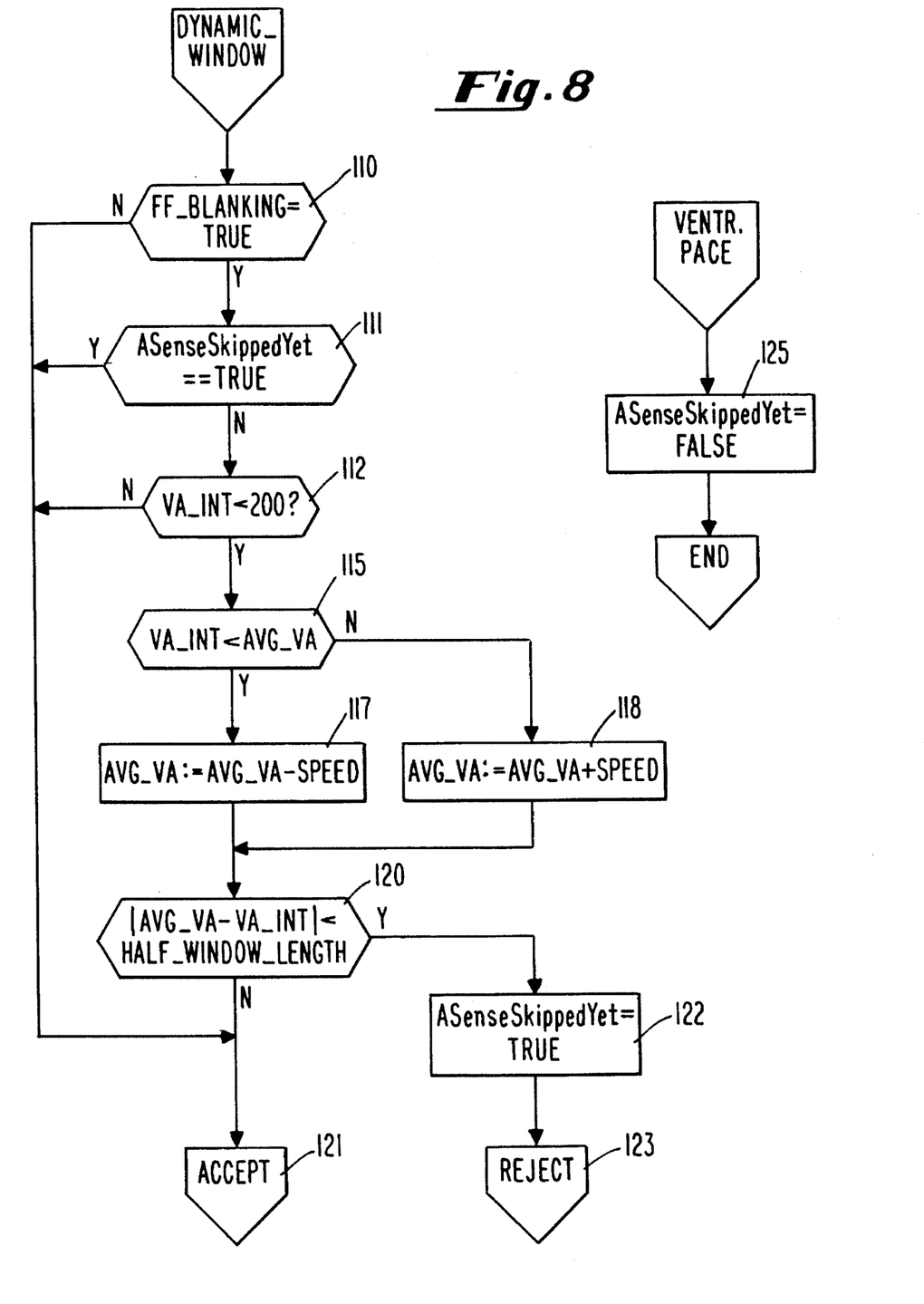
FIG. 8 is a flow diagram of the dynamic window routine which adjusts the dynamic window and determines whether an atrial sense is within or outside of that window.

Referring now to FIG. 8, the dynamic window routine is entered at block 110. If the FF blanking flag is not at true, but is set to false, this means that the window has been switched off, i.e., been made inactive. An example of this is seen at block 136, FIG. 10. In this case, the pacemaker is operating in an asynchronous mode and is not tracking atrial signals, so the routine simply jumps to the end, accepting the signal for interpretation at block 121. Assuming that the FF blanking flag is set to true, the routine goes to block 111 and determines whether the A sense skipped yet flag is set to true. If yes, this means that there has been an AS captured in the dynamic blanking window without any VP intervening before the atrial sense being examined. This could happen, for example, during an episode of 1:2 pacing. In this situation, there has already been one AS in the blanking window, and accordingly the blanking window is not to be adjusted. For this reason, the routine skips to the end and accepts the signal for further interpretation.

Still referring to block 111, if the A sense skipped yet flag is not true, the routine goes to block 112 and determines whether VA_int is <200 ms. If no, this means that the A sense has come after the window range, and accordingly the routine skips to the end and accepts the signal for further interpretation. If, however, VA_int is <200 ms, the routine goes to block 115 and determines whether VA_int is less than average Avg_VA. Avg_VA is a running average of the VA interval for senses within the window range, and represents the approximate position where the pacemaker wants to center the dynamic tracking window. If the window interval is less than Avg_VA, the routine branches to block 117 and adjusts Avg_VA by subtracting an arbitrary value indicated as "speed." This value determines the speed by which the window moves to the location of a repetitive atrial sense such as an FFRS. By way of illustration, the value of this factor can be 0.4 ms. Alternately, if at 115 it is determined that VA_int is not less than Avg_VA, the routine goes to block 118 and increments Avg_VA by the factor speed. Then, at 120, the absolute value of the difference between Avg_VA and VA interval is compared to half the window length. If this absolute value is less than half the window length, this means that the A sense has occurred within the window, and should be rejected. The routine branches to block 122 where the A sense skipped yet flag is set equal to true, and then exits through the reject path, at 123. Note, however, that following a VP the A sense skipped yet flag is set back to false at block 125. If the absolute value of Avg_VA−VA_int is not less than half a window length, this means the A sense is outside of the window, and is not captured. In this situation, the routine exits through the accept path, at 121.

As discussed above, despite the use of a small dynamic blanking window, it is still possible for the pacemaker to find itself in 1:2 tracking. Theoretically, this situation may last for days, and accordingly it is desirable to be able to detect this situation and provide a pacemaker response which enables getting out the 1:2 tracking. There are basically two ways that the pacemaker can find itself in 1:2 tracking: the sinus rate suddenly doubles, or the ventricular rate becomes half the sinus rate when the ventricular rate flywheels down in response to a jump in the sinus rate to a tachy level. In the discussion that follows the effect of an interference delay is neglected.

The criteria for initiating a 1:2 test consists of the following rules:
1. Senses are blanked in the dynamic blanking window;
2. The pacer is in synchronous operation;
3. The atrial rate is high enough that senses occurring at twice the present sensed rate can fall in the dynamic window, i.e., AA interval <=2* (AV delay+window position); and
4. There is a pattern of atrial senses following ventricular paces. e.g., for the last 32 VP, at least 26 were followed by an AS.

It is to be noted that in a VDD system, 1:2 tracking is not so easily obtained with a dynamic blanking window. However, in a DDD system that has atrial sync paces, such ASPs facilitate 1:2 tracking. Briefly, an ASP can result in a VP which positions the window just right for blanking a next P wave, thus setting up 1:2 tracking. Accordingly, in a preferred embodiment of this invention, the pacemaker constantly monitors the AA intervals and determines when the rate is classified as a tachy rate. When this happens, the dynamic blanking after delivery of an ASP is deactivated. After one or more cycles, dynamic blanking is again activated.

Figure 9:
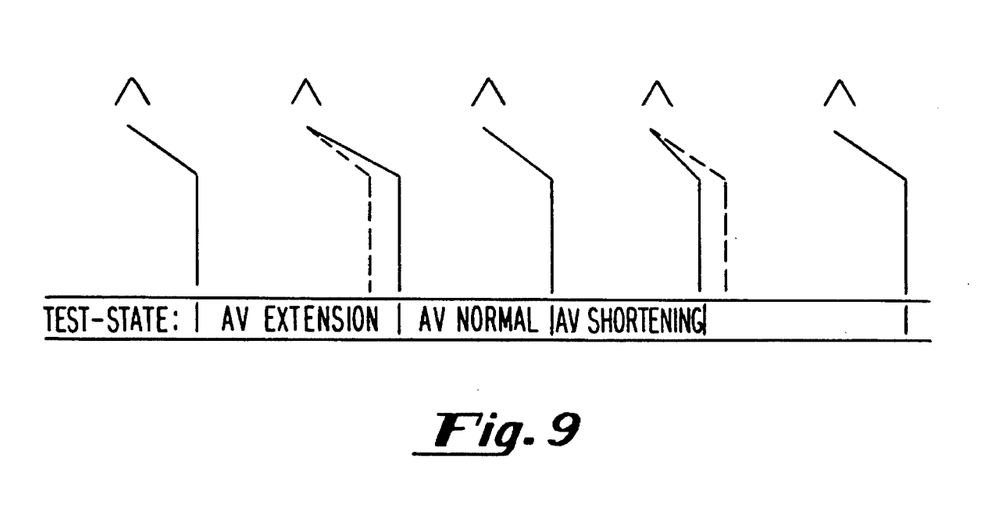
FIG. 9 is a timing diagram illustrating AV modulation for carrying out a 1:2 test in accordance with this invention.

Referring now to FIG. 9, there is illustrated a timing diagram for a 1:2 test sequence. The test sequence comprises a first AV extension, one normal cycle to prevent an unacceptably short VV interval, and then one cycle with a shortened AV delay. The extension or shortening may be in the range of 25–90 ms. If, in any one of the cycles, a P wave is revealed and identified as a tachycardia, the pacemaker immediately switches to synchronous from asynchronous operation, and thus cancels further testing. After the test has been performed, the pacemaker determines whether async has been detected, and if it has been, it increments a counter representing the number of times that the async mode has been produced by modulation (Nr ASync By Mod). If async has not been detected as a result of the test, then the counter is decreased. When, as a result of a number of such 1:2 test sequences, the counter becomes 3, the FF blanking flag is switched off for n intervals, or cycles, e.g., 15 intervals. During this time, the pacemaker sees all the tachy P-waves, and responds by pacing the ventricle asynchronously at a flywheel rate which ramps down to a lower pacing limit. As seen in the rate diagram of FIG. 11, the physiological band between DPL and DTL consequently drops. When the dynamic blanking window is switched on again, DTL is below the half tachy rate and thus 1:2 tracking is avoided. Synchronous tracking will be reinitiated when the tachycardia episode terminates.

Figure 10:
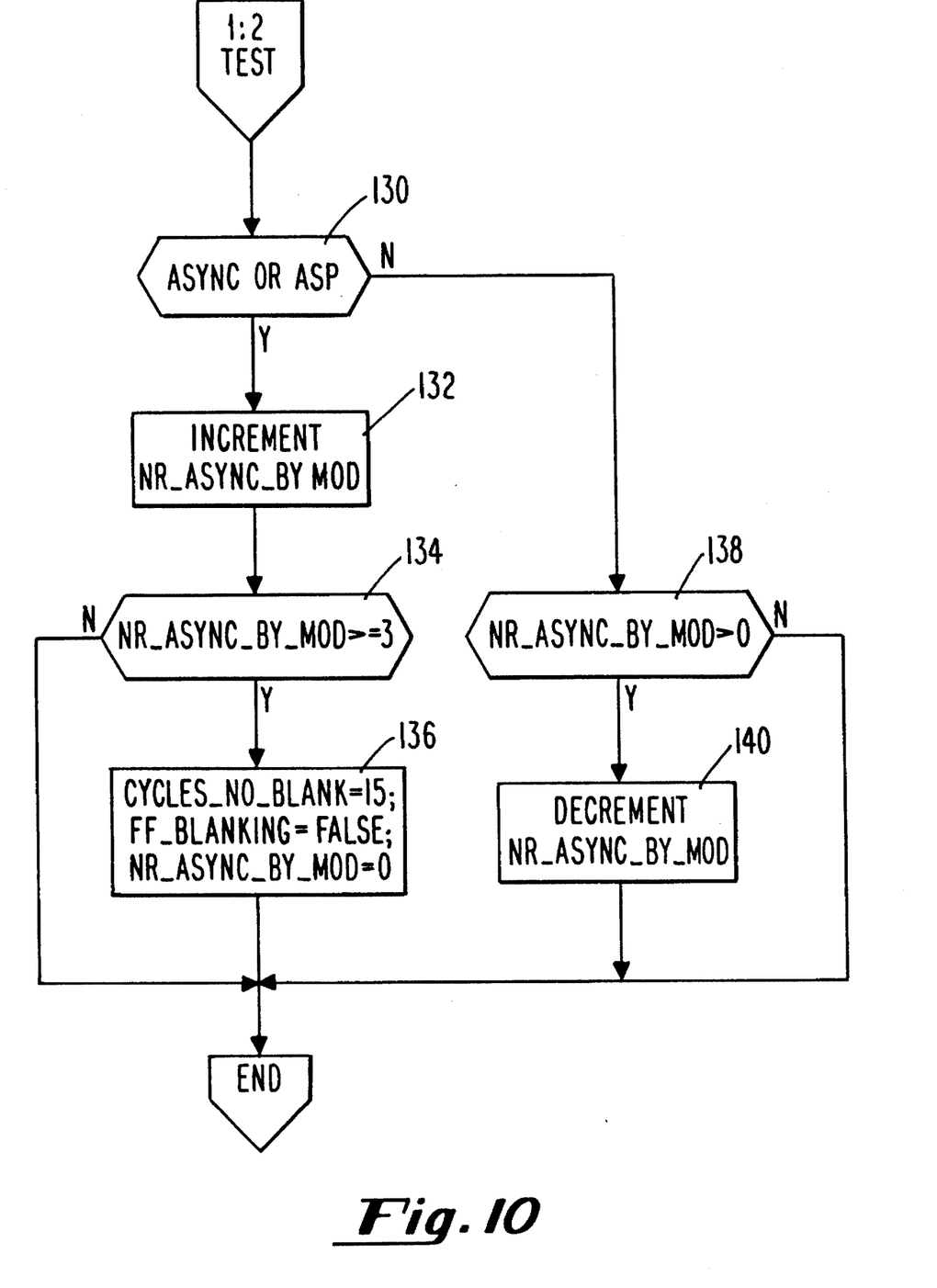
FIG. 10 is a flow diagram illustrating the conditions under which the dynamic window is switched off as a result of a 1:2 test.

Referring now to FIG. 10, there is shown a simplified flow diagram illustrating a routine for switching off the dynamic window as a result of 1:2 testing. The routine of FIG. 10 is entered following a 1:2 test sequence, carried out in accordance with the timing diagram of FIG. 9. At block 130, it is determined whether the pacemaker has delivered an asynchronous VP, or an ASP. If yes, this means that a P-wave was found within the window range but outside of the dynamic window. Under these circumstances, the routine goes to block 132 and increments a Nr Async By Mod counter. Then at block 134, it is determined whether the Nr Async By Mod counter is greater than or equal to 3. If no, the routine exits; however, if it is greater than or equal to 3, this means that repeated 1:2 tests have determined a tachy situation that was being tracked. The routine goes to block 136 and sets the pacemaker to "No Blank" for the next 15 cycles, i.e., it de-activates the dynamic window. It also resets the Nr Async By Mod count to 0, and sets the FF blanking flag to false.

Returning to block 130, if there has been no async or ASP response, this means that no P-wave was revealed after AV modulation. The routine then branches to block 138, and determines if the Nr Async By Mod counter has a setting greater than 0. If no, the routine jumps to the end; but if yes, the routine goes to block 140 and decrements the Nr Async By Mod counter by 1. This decrementing feature ensures that the dynamic window is not switched off unless there has been a strong pattern of P-waves discovered by the 1:2 sequences, such as to result in a determination of 1:2 pacing.

During this period, none of the senses are blanked by the dynamic blanking window, and consequently all are interpreted as tachy senses (TAS). With the pacemaker programmed to the "dynamic mode" the physiological band (between DPL and DTL) drops as long as the tachy condition persists. When the dynamic blanking window is switched on again, after n cycles, most likely the physiological band has been dropped sufficiently that the dynamic tracking limit is below the half tachy rate (1:2 rate), such that the pacemaker stays in asynchronous operation. This is illustrated in the rate diagram of FIG. 11.

It is thus seen that the use of a small dynamic blanking window instead of a fixed PVARP reduces the problem of blanking P-waves, and thus gives the pacemaker a greater ability to sense atrial tachycardia. In the less likely event that some P-waves are blanked, AV modulation is used to uncover P-waves while maintaining selective blanking of FFRS. If conditions suggest that the use of the dynamic window may hide one or more P-waves, provision is made to deactivate the window so as to effectively deactivate all but a small portion of the PVARP function for a limited number of pacemaker cycles.

The above description sets forth the preferred embodiment of the invention. However, it is to be understood that additional refinements are possible, and within the scope of the invention. For example, the pacemaker can use two different blanking windows, one for V sense situations and one for V pace situations. Since, as noted above, FFRS is statistically different depending upon whether the ventricular event has been a VP or a VS, the pacemaker desirably maintains a dynamic blanking window corresponding to each, and selects the appropriate window following each V event.

Other operating variables may be subject to additional control, within the scope of the invention. In connection with FIG. 8, reference has been made to the "speed" factor for adjusting the position of tile blanking window. A slow speed has the advantage that temporary disturbances will not affect tile window position, but the disadvantage of taking a long time to move the window to the correct position; a fast speed has the advantage of moving the window quickly, but the disadvantage that the window could be improperly shifted due to temporary disturbances. Speed can be controlled in these 3 ways: (1) speed can be fixed; (2) speed is set to a fast value during an initial learning period after implantation, and then switched to a slower value; and (3) whenever speed is made fast, it is then gradually ramped down to a slow value. Whatever technique is used, it is important to note that the speed can be controlled, either dynamically or by external programming.

Another variable subject to additional control is window length, or duration. Window length can be fixed, e.g. programmable in steps of 6.4 ms. Alternately, a VA histogram derived from senses in the blanking window range (e.g., 50–200 ms). may be used to determine at what VA intervals most senses are found. Thus, for 24 bins of 6.4 ms, if a high percentage of intervals are found in N adjacent bins, then the blanking interval can be N×6.4 ms, or perhaps (N±1) (6.4 ms).

Likewise, activation and deactivation of the blanking window can be controlled as a function of the monitored percentage of PAC and FFRS events. Thus, when less than a given percentage of senses within the range are blanked, this indicates these senses are primarily PAC's, not FFRS, and blanking can be switched off-deactivated. Similarly, when the pacemaker recognizes a great number of senses distributed randomly in the blanking range, such as due to tachycardia, either the pacemaker can inhibit window shifting, or minimize the effect of the random senses on the window shifting.

There is thus disclosed an improved pacemaker for enabling a minimized effective PVARP, while at the same time enabling efficient detection and blanking of FFRS.

What is claimed is:

1. A dual chamber pacemaker comprising atrial sense means for sensing atrial signals (AS), ventricular pace means for generating ventricular pace pulses (VP) for delivery to a patient's ventricle, and PVARP means for establishing a post-ventricular atrial refractory period (PVARP) which occurs after a delivered VP, wherein said PVARP means comprises:

range means for defining a range of time within said PVARP, dynamic window means for dynamically timing a blanking window within said range, said dynamic window means having dynamic adjust means for adjusting the timing of said blanking window to track AS events, and reject means for rejecting an AS signal which occurs within said blanking window but not an AS signal which occurs outside of said blanking window and within said range.

2. The pacemaker as described in claim 1, wherein said reject means comprises comparison means for comparing the timing of an AS to the timing of said blanking window.

3. The pacemaker as described in claim 2, wherein said dynamic window means times out said blanking window for a predetermined duration within a range of 0 to 100 ms.

4. The pacemaker as described in claim 3, wherein said dynamic adjust means has increment means for moving said blanking window by a predetermined increment as a function of said comparison.

5. The pacemaker as described in claim 1, wherein said dynamic adjust means further comprises modulating means for modulating the timing of said blanking window in accord with a predetermined pattern of modulation.

6. The pacemaker as described in claim 5, further comprising sync means to control said ventricular pace means to generate a VP which follows an AS by a predetermined AV interval, and wherein said dynamic window means times said blanking window in a timed relation to said VP, and wherein said modulating means modulates said AV interval, thereby modulating said blanking window.

7. The pacemaker as described in claim 6, further comprising storage means for storing predetermined test criteria, and test means for determining the occurrence of said criteria and for initiating said modulating means in response to the occurrence of said predetermined criteria.

8. The pacemaker as described in claim 5, comprising 1:2 block means for determining an occurrence of 1:2 block caused by every other AS occurring during said PVARP window, and means for initiating said modulation means to modulate the timing of said dynamic window in response to determination of 1:2 block.

9. The pacemaker as described in claim 5, comprising means for determining whether a signal rejected by said reject means was a far-field R wave sense.

10. A dual chamber pacemaker comprising atrial sense means for sensing atrial signals (AS), ventricular pace means for generating ventricular pace pulses (VP) for delivery to a patient's ventricle, and PVARP means for establishing a post-ventricular atrial refractory period (PVARP) which occurs after a delivered VP, wherein said PVARP means comprises:

range means for establishing a post-ventricular atrial window range, within said PVARP time interval, tracking means for tracking each atrial sense that occurs within said post-ventricular atrial window range, window means for determining a dynamic blanking window which follows each said tracked atrial sense, and reject means for rejecting an atrial sense that occurs within said dynamic blanking window, and accept means for accepting an AS signal that occurs within said post-ventricular atrial window range but outside of said dynamic blanking window.

11. The pacemaker as described in claim 10, wherein said tracking means comprises timing means for determining the timing of each atrial sense that occurs within said post-ventricular atrial window range and means for maintaining a running average of said timed atrial senses, and wherein said window means adjusts said window to follow said maintained average.

12. The pacemaker as described in claim 10, further comprising means responsive to an occurrence of an atrial sense within said dynamic blanking window for determining whether said sense was a sensed atrial signal or a far-field R-wave.

13. The pacemaker as described in claim 10, comprising sync means for controlling said ventricular pace means to deliver pace pulses in synchronous relation to sensed atrial signals, situation means to determine a situation where the pacemaker is synchronously tracking alternate P-waves, and response means for responding to such situation.

14. The pacemaker as described in claim 13, wherein said response means comprises modulation means for modulating said dynamic blanking window relative to the preceding atrial event.

15. A dual chamber pacemaker comprising atrial sense means for sensing atrial signals (AS), ventricular pace means for generating ventricular pace pulses (VP) for delivery to a patient's ventricle, and atrial sense reject means for rejecting any atrial sense signal which occurs under predetermined conditions and within a predetermined post-ventricular interval following a said VP, said reject means comprising timing means for timing an AS signal which occurs within said interval and obtaining a measure of said timing, window means for adjusting a dynamic window of a predetermined interval to move in accordance with said timing measure, and said reject means having means for determining when an AS is within said dynamic window and rejecting only an AS determined to be within said window.

16. A dual chamber pacemaker comprising atrial sense means for sensing atrial signals, ventricular pace means for generating ventricular pace pulses for delivery to a patient's ventricle, sync means for controlling said pace means to deliver ventricular pace pulses in synchronized relation to sensed atrial signals, and PVARP means for blanking signals received from said atrial sense means during at least a predetermined interval following delivery of a ventricular pace pulse, further comprising test means for testing to determine when said pacemaker is delivering synchronized ventricular pace pulses following only every other one of said sensed atrial signals (1:2 tracking), and response means for controlling the generation of pulses by said ventricular pace pulse means so as to avoid said 1:2 tracking.

17. A dual chamber pacemaker comprising atrial sense means for sensing atrial signals, ventricular pace means for generating ventricular pace pulses for delivery to a patient's ventricle, sync means for controlling said pace means to deliver ventricular pace pulses in synchronized relation to sensed atrial signals, and PVARP means for blanking signals received from said atrial sense means during at least a predetermined interval following delivery of a ventricular pace pulse, further comprising control means for controlling said PVARP means to be active or inactive, said control means having event means for determining when at least one predetermined event has occurred and for controlling said PVARP means to be inactive following a said determined event.

18. The pacemaker as described in claim 17, wherein said control means has count means for counting a predetermined number of pacemaker cycles and means for controlling said PVARP means to be inactive for a predetermined number of said cycles following a said determined event.

19. The pacemaker as described in claim 18, wherein said number is in a range of 1–100.

20. The pacemaker as described in claim 17, wherein said PVARP means comprises fixed blanking means for providing a fixed post ventricular atrial blanking period of no more than about 50 ms.

21. The pacemaker as described in claim 20, wherein said PVARP means further comprises blanking window means for blanking atrial senses that fall within a dynamic blanking window having a duration of up to 100 ms, said blanking window means having adjust means for moving said dynamic window within a range of about 50–200 ms following a ventricular event.

* * * * *

UNITED STATES PATENT AND TRADEMARK OFFICE
CERTIFICATE OF CORRECTION

PATENT NO. : 5,549,647
DATED : August 27, 1996
INVENTOR(S) : Gustaaf A.P. Stoop et al.

It is certified that error appears in the above-indentified patent and that said Letters Patent is hereby corrected as shown below:

```
Col. 9, line 21, "tile blanking should be
    --the blanking--.
```

Signed and Sealed this

Fourth Day of November, 1997

Attest:

BRUCE LEHMAN

*Attesting Officer*   *Commissioner of Patents and Trademarks*